United States Patent [19]

Weill et al.

[11]  4,433,157
[45]  Feb. 21, 1984

[54] PROCESS FOR MANUFACTURING ANHYDRIDES OF ALKENYL DICARBOXYLIC ACIDS

[75] Inventors: Jérome Weill; Jacques Garapon, both of Lyons; Bernard Sillion, Rocquencourt, all of France

[73] Assignee: Institut Francais du Petrole, Rueil-Malmaison, France

[21] Appl. No.: 377,114

[22] Filed: May 11, 1982

[30] Foreign Application Priority Data

May 11, 1981 [FR] France ............................. 81 09473

[51] Int. Cl.$^3$ .......................................... C07D 307/60
[52] U.S. Cl. .................................. 549/255; 260/546; 549/231; 549/232
[58] Field of Search ................... 549/255, 231, 232; 260/246

[56] References Cited

U.S. PATENT DOCUMENTS

| | | | |
|---|---|---|---|
| 2,628,942 | 2/1953 | Morris et al. | 252/49.7 |
| 2,634,256 | 4/1953 | Sparks et al. | 260/78.4 |
| 3,172,892 | 3/1965 | Le Suer et al. | 260/326.5 |
| 3,864,270 | 2/1975 | Cullen et al. | 252/51.5 A |
| 3,927,041 | 12/1975 | Cengel et al. | 260/346.8 |
| 3,954,812 | 5/1976 | Puskas et al. | 260/346.8 R |
| 4,235,786 | 11/1980 | Wisotsky | 549/255 |
| 4,255,340 | 3/1981 | Powell | 549/261 X |

FOREIGN PATENT DOCUMENTS

| | | |
|---|---|---|
| 2257604 | 8/1975 | France . |
| 2273014 | 12/1975 | France . |
| 949981 | 2/1964 | United Kingdom . |
| 1356802 | 6/1974 | United Kingdom . |

*Primary Examiner*—Richard Raymond
*Attorney, Agent, or Firm*—Millen & White

[57] ABSTRACT

A process for manufacturing an alkenyl dicarboxylic acid, anhydride comprises reacting at least one halogenated polyolefin with at least one unsaturated dicarboxylic acid anhydride in substantially stoichiometrical proportion, in the presence of a minor proportion of at least one organic compound containing at least one double bond bearing at least one electron attracting substituent.

9 Claims, No Drawings

PROCESS FOR MANUFACTURING ANHYDRIDES OF ALKENYL DICARBOXYLIC ACIDS

BACKGROUND OF THE INVENTION

The invention concerns a process for manufacturing alkenyl dicarboxylic acid anhydrides.

The alkenyl dicarboxylic compounds, acids or anhydrides, are important starting materials for manufacturing additives for fuels and lubricants. The products usually employed consist of a hydrocarbon chain with a mass of from 200 to 2000, on which is attached at least one succinic group.

Manufacturing processes starting from an olefin oligomer and maleic anhydride are known in the prior art. The condensation is performed at a temperature higher than 200° C. and the reaction time must be sufficiently long to obtain a conversion of about 75%. Processes of this type are described, particularly in the U.S. Pat. Nos. 2,628,942 and 2,634,256.

To improve the conversion, it has been proposed, in French Pat. No. 2,257,604, to use maleic anhydride in excess; however, even in that case, the condensation temperature remains higher than 200° C., the reaction time is about 20 hours and the process necessitates the step of removing excess maleic anhydride at the end of the reaction.

It has thereafter been proposed to prepare compounds of the same nature by condensing maleic anhydride with a previously chlorinated polyolefin containing approximately one chlorine atom per molecule of the polyolefin. This technique is described, for example, in the British Pat. No. 922,831, corresponding to U.S. Pat. No. 3,172,892. The reaction time is shorter and the operative temperature is not as high as when condensing the polyolefin itself. The secondary reactions which result in the formation of polymeric resins are also avoided. It is also mentioned that the unsaturated anhydrides decompose from 150° C. upward.

Attempts have been made to simplify this process, particularly by performing the chlorination and the condensation in one step: for example, the British Pat. No. 949,981 discloses the chlorination of a mixture of polyisobutane with maleic anhydride at a temperature of 190° to 210° C., the condensation time being, under these conditions, 10 h.

The British Pat. No. 1 356 802 describes the addition of iodine to the reaction mixture after a 25% conversion; however, under these conditions, the reaction temperature is 215° C. and the reaction must be continued up to 24 hours to obtain satisfactory conversions.

The French Pat. No. 2 273 014 shows that bromine can be used to catalyze the reaction, but the reaction temperature is 240° C. in the described conditions.

In a number of patents, the halogens used to catalyze the reaction of the polyolefins with maleic anhydride are not used in the free state but combined with other organic molecules; for example, the U.S. Pat. No. 3,927,041 describes the use of a 1,3-dibromo-5,5-dialkyl hydandoin and the U.S. Pat. No. 3,954,812 shows that acid chlorides, chloro-acids and N-bromosuccinimide may be used as halogen generators.

The mechanism by which the halogen compounds operate has not been perfectly explained, but it is probable that the polyolefin halogenates and then dehydrohalogenates prior to the condensation with the anhydride: this path is described in the U.S. Pat. No. 3,864,270 where is is shown that the polyolefin can be chlorinated at between 20° and 150° C., then dehydrochlorinated at between 150° and 250° C., preferably at 235° C. for 5 hours. After these operations, maleic anhydride is condensed for 6 hours at about 100° C.

It is clear that the dehydrochlorination step is the step which necessitates the higher temperature.

SUMMARY OF THE INVENTION

It has now been found that the dehydrochlorination of the chlorinated polyolefins can be obtained under mild conditions with the use of organic catalysts. The invention is based on the fact that these catalysts work in the presence of maleic anhydride; their use in the condensation of a halogenated polyolefin with an unsaturated cyclic anhydride results in a simplified process for manufacturing alkenyl dicarboxylic anhydrides.

DETAILED DISCUSSION

The main advantages of the catalytic process of the invention over prior art processes resides in the fact that it permits the operation to be conducted at lower temperatures and the conversion to run at an increased velocity, leading to enhanced yields of the desired alkenyl dicarboxylic anhydride.

As a rule, the process of the invention comprises the reaction of at least one halogenated polyolefin with a substantially stoichiometrical proportion of at least one unsaturated dicarboxylic acid anhydride, in the presence of a minor proportion of an organic catalyst as defined hereinbelow. The reaction temperature may be, for example, from 150° to 200° C.

The organic catalysts used in the process of the invention (which make the dehydrochlorination of the polyolefins easier) are compounds containing a double bond whose electronic density is lower than that of the conventional olefins, these double bonds being substituted with electron-attracting elements. These compounds are further selected from those which react with difficulty in the ene reaction of this synthesis.

Among the compounds which have an effect on the dehydrochlorination of the halogenated polyolefins, the following may be mentioned as examples: the halogenoquinones, the cyanoquinones, the haogenomaleic anhydrides and the polycyano-olefins. Among all these compounds, dichloromaleic anhydride has proved to be one of the most advantageous.

The catalyst can be used in a proportion of 0.5 to 5% by mole. The dehydrohalogenation temperature which is with the technique of the invention is preferably from 170° to 185° C.

The reaction is practically terminated after about 7 to 10 hours.

The halogenated polyolefins to be used within the scope of the present invention are obtained by halogenation of polyolefins of the polyisobutene or polypropylene type having a molecular weight between 200 and 3000, the halogenation rate being preferably between 0.8 and 1.5 halogen atom per molecule of polyolefin. The halogen may be chlorine, bromine or iodine; for economic reasons, the use of chlorine is preferred.

Finally, among suitable anhydrides of unsaturated dicarboxylic acids, the most commonly employed is maleic anhydride.

The following examples illustrate the invention but are not to be construed as limitative in any respect.

EXAMPLE 1

Manufacture of chlorinated polyisobutene 5 moles (4775 g) of chlorinated polyisobutene of average molecular weight 955 are prepared by passing 5 moles (355 g) of gaseous chlorine through 5 moles (4600 g) of polyisobutene of average molecular weight 920, at 80° C., in the dark. The resultant chlorinated polyisobutene contains 3.6% b.w. of chlorine, which corresponds to about 1 chlorine atom per molecule of polymer.

EXAMPLE 2

Comparison example 1 mole (955 g) of the resultant chlorinated polyisobutene is heated to 180° C. Nitrogen is continuously bubbled therethrough to titrate the released hydrochloric acid. After 1 hour, 7.5% of the theoretical maximum quantity are titrated and, after 7 hours, the reaction is terminated and only 34% are titrated, which shows that the types of chlorine spontaneously releasable at this temperature represent 34% of the total amount of chlorine present in the chlorinated polyisobutene.

EXAMPLE 3

Comparison example

The same experiment is renewed by heating, also at 180° C., 1 mole (955 g) of the same chlorinated polyisobutene, in the presence of 1.1 mole (108 g) of maleic anhydride. After 1 hour, 24% of the theoretical maximum quantity of hydrochloric acid are titrated, and, after 8 hours, the reaction is terminated with only 50% of the maximum amount titrated, which shows that the types of chlorine releasable at this temperature in the presence of maleic anhydride represent 50% of the total chlorine amount. The amount of alkenyl dicarboxylic anhydride formed in this reaction is 0.45 mole (yield: 45% by mole).

EXAMPLE 4

Demonstration of the effect of dichloromaleic anhydride

The same experiment is performed by heating at 180° C. 1 mole (955 g) of the same chlorinated polyisobutene in the presence of 1.1 mole (184 g) of dichloromaleic anhydride. After 1 hour, 80% of the theoretical maximum amount of hydrochloric acid is found and, after 3 hours, the reaction is terminated and 100% is found; this shows that all the types of chlorine present in chlorinated polyisobutene can be liberated at this temperature in the presence of dichloromaleic anhydride.

EXAMPLE 5

Effect of a decreased proportion of dichloromaleic anhydride

The same experiment is performed by heating at 180° C. 1 mole (955 g) of the same chlorinated polyisobutene in the presence of 0.055 mole (9 g) of dichloromaleic anhydride. After 1 hour, 30% of the theoretical maximum amount of hydrochloride acid is titrated, and after 10 hours, the reaction is terminated and 95% of the theoretical amount is found, which shows that a very low amount of dichloromaleic anhydride is able to liberate all types of chlorine. The amount of alkenyl dicarboxylic anhydride is then lower than 0.005 mole, which shows that dichloromaleic anhydride is not liable to further react with dehydrochlorinated chlorinated polyisobutene.

EXAMPLE 6

Manufacture of alkenyl dicarboxylic anhydride according to the invention

The same experiment is performed by heating at 180° C. 1 mole (955 g) of the same chlorinated polyisobutene in the presence of 1.1 mole (108 g) of maleic anhydride and 0.055 mole (9 g) of dichloromaleic anhydride. In 1 hour, 37% of the theoretical maximum amount of hydrochloric acid is titrated, and, after 7 hours, the reaction is terminated and 95% is titrated. The amount of alkenyl dicarboxylic anhydride is then 0.91 mole (yield: 91% by mole).

EXAMPLE 7

Manufacture of alkenyl dicarboxylic anhydride according to the invention

The same experiment is performed by heating at 180° C. 1 mole (955 g) of the same chlorinated polyisobutene in the presence of 1.1 mole (108 g) of maleic anhydride and 0.0055 mole (0.9 g) of dichloromaleic anhydride. After 1 hour, 26% of the theoretical maximum amount of hydrochloric acid is titrated, and, after 7 hours, 55% is found. The amount of alkenyl dicarboxyl anhydride is then 0.50 mole (yield: 50% by mole).

EXAMPLE 8

Manufacture of alkenyl dicarboxylic anhydride according to the invention

The same experiment is performed by heating at 180° C. 1 mole (955 g) of the same chlorinated polyisobutene in the presence of 1.1 mole (108 g) of maleic anhydride and 0.011 mole (1.8 g) of dichloromaleic anhydride. After 1 hour, 27% of the theoretical maximum quantity of hydrochloric acid is titrated, and after 7 hours, 62% is titrated. The amount of alkenyl dicarboxylic anhydride is then 0.59 mole (yield: 59% by mole).

EXAMPLE 9

Manufacture of alkenyl dicarboxylic anhydride according to the invention

The same experiment is performed by heating at 180° C. 1 mole of the same chlorinated polyisobutene (955 g) in the presence of 1.1 mole (108 g) of maleic anhydride and 0.033 mole (5.4 g) of dichloromaleic anhydride. After 1 hour, 30% of the theoretical maximum amount of hydrochloric acid is titrated, and after 7 hours, 75% is titrated. The amount of alkenyl dicarboxylic anhydride is then 0.71 mole (yield: 71% by mole).

EXAMPLE 10

Manufacture of alkenyl dicarboxylic anhydride according to the invention

The same experiment is repeated by heating at 180° C. 1 mole of the same chlorinated polyisobutene (955 g) in the presence of 1.1 mole (108 g) of maleic anhydride and 0.055 mole (13.5 g) of ortho tetrachloroquinone. After 1 hour, 28% of the theoretical maximum amount of hydrochloric acid is titrated, and after 7 hours, 65% is titrated. The amount of alkenyl dicarboxylic anhydride is then 0.62 mole (yield: 62% by mole).

What is claimed is:

1. In a process for manufacturing an alkenyl dicarboxylic acid anhydride, by reacting at least one halogenated polyolefin with at least one unsaturated dicarboxylic acid anhydride in substantially stoichiometric proportions, the improvement comprising effecting said reaction at a temperature of 150°–200° C., in the presence of a minor proportion of at least one organic compound containing a double bond bearing at least one electron-attracting substituent and having a lower electron density than an unsubstituted double bond, said organic compound being substantially unreactive with dehydrohalogenated halogenated polyolefin.

2. A process according to claim 1, wherein said organic compound is a halogenoquinone, a cyanoquinone, a halogeno-maleic anhydride or a polycyanoolefin.

3. A process according to claim 2, wherein said organic compound is dichloro-maleic anhydride.

4. A process according to claim 1, wherein said organic compound is used in a molar proportion of 0.5 to 5% with respect to said unsaturated dicarboxylic acid anhydride.

5. A process according to claim 1, wherein said reaction temperature is 170°–185° C.

6. A process according to claim 1, wherein said halogenated polyolefin is obtained by halogenation with chlorine, bromine or iodine of a polyolefin of molecular weight from 200 to 3000, the halogenation rate being about 0.8 to 1.5 halogen atom per molecule of polyolefin.

7. A process according to claim 6, wherein said polyolefin is a polyisobutene or a polypropylene.

8. A process according to claim 6, wherein said halogenated polyolefin is a chlorinated polyisobutene.

9. A process according to claim 1, wherein said unsaturated dicarboxylic acid anhydride is maleic anhydride.

* * * * *